DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MARCH 27, 1973

908 O.G. 788

T908,003

PROCESS FOR STABILIZED POLYETHERS

Michael Kokorudz, 17994 Parke Lane,
Grosse Ile, Mich. 48138

Filed June 21, 1971, Ser. No. 155,329
Int. Cl. C07c *43/30*
U.S. Cl. 260—615 A
No Drawing. 8 Pages Specification

The process for preparing hydroxyl terminated polyalkylene polyethers stabilized by conversion to acetals through reaction with alphahaloalkyl alkyl ethers is improved by heat treating the acetals in the presence of an alkali carbonate to eliminate free hydrohalide acid and oxonium hydrogen halide.